United States Patent
Ludwin et al.

(10) Patent No.: US 10,555,672 B2
(45) Date of Patent: Feb. 11, 2020

(54) USING LOCATION AND FORCE MEASUREMENTS TO ESTIMATE TISSUE THICKNESS

(71) Applicant: BIOSENSE WEBSTER (ISRAEL) LTD., Yokneam (IL)

(72) Inventors: Doron Moshe Ludwin, Haifa (IL); Assaf Govari, Haifa (IL); Aharon Turgeman, Zichron Ya'acov (IL); Yohai Makbily, Haifa (IL); Eliahu Zino, Atlit (IL)

(73) Assignee: Biosense Webster (Israel) Ltd., Yokneam (IL)

(*) Notice: Subject to any disclaimer, the term of this patent is extended or adjusted under 35 U.S.C. 154(b) by 304 days.

(21) Appl. No.: 15/678,714

(22) Filed: Aug. 16, 2017

(65) Prior Publication Data

US 2017/0340207 A1    Nov. 30, 2017

Related U.S. Application Data

(63) Continuation of application No. 13/680,496, filed on Nov. 19, 2012, now abandoned.

(51) Int. Cl.
| | | |
|---|---|---|
| *A61B 5/00* | (2006.01) | |
| *A61B 5/107* | (2006.01) | |
| *A61B 5/06* | (2006.01) | |
| *A61B 5/02* | (2006.01) | |
| *A61B 5/0215* | (2006.01) | |

(52) U.S. Cl.
CPC ........ *A61B 5/0053* (2013.01); *A61B 5/02007* (2013.01); *A61B 5/062* (2013.01); *A61B 5/1075* (2013.01); *A61B 5/1076* (2013.01); *A61B 5/6847* (2013.01); *A61B 5/6852* (2013.01); *A61B 5/6885* (2013.01); *A61B 5/02156* (2013.01); *A61B 5/6869* (2013.01); *A61B 5/6876* (2013.01); *A61B 2560/0223* (2013.01); *A61B 2562/0247* (2013.01)

(58) Field of Classification Search
CPC ... A61B 5/0053; A61B 5/02007; A61B 5/062; A61B 5/1075; A61B 5/1076; A61B 5/6847; A61B 5/6852; A61B 5/6885
See application file for complete search history.

(56) References Cited

U.S. PATENT DOCUMENTS

| | | |
|---|---|---|
| 5,391,199 A | 2/1995 | Ben-Haim |
| 5,433,215 A | 7/1995 | Athanasiou |

(Continued)

FOREIGN PATENT DOCUMENTS

| | | |
|---|---|---|
| AU | 2013257409 A1 | 5/2018 |
| EP | 1 743 575 A2 | 1/2007 |

(Continued)

OTHER PUBLICATIONS

European Search Report dated Mar. 21, 2014 from corresponding European Patent Application No. 13193323.6.

*Primary Examiner* — Max F Hindenburg
(74) *Attorney, Agent, or Firm* — Vincent J. Serrao

(57) ABSTRACT

A method, including pressing a distal end of a medical probe against a wall of a body cavity, and receiving from the probe first measurements of a force exerted by the distal end on the wall. The method also includes receiving from the probe second measurements indicating a displacement of the wall in response to the force. The method further includes estimating a thickness of the wall based on the first and the second measurements.

9 Claims, 5 Drawing Sheets

(56) References Cited

U.S. PATENT DOCUMENTS

| | | |
|---|---|---|
| 5,503,162 A | 4/1996 | Athanasiou et al. |
| 5,673,708 A | 10/1997 | Athanasiou et al. |
| 5,876,357 A | 3/1999 | Tomer |
| 6,239,724 B1 | 5/2001 | Doron et al. |
| 6,332,089 B1 | 12/2001 | Acker et al. |
| 6,484,118 B1 | 11/2002 | Govari |
| 6,585,666 B2 | 7/2003 | Suh et al. |
| 6,618,612 B1 | 9/2003 | Acker et al. |
| 6,690,963 B2 | 2/2004 | Ben-Haim et al. |
| 7,267,649 B2 | 9/2007 | Zdeblick et al. |
| 7,708,692 B2 | 5/2010 | Kato et al. |
| 7,947,001 B1 | 5/2011 | Sarvazyan |
| 8,062,236 B2 | 11/2011 | Soltz |
| 8,131,379 B2 | 3/2012 | Hauck |
| 8,523,787 B2 | 9/2013 | Ludwin et al. |
| 8,535,308 B2 | 9/2013 | Govari et al. |
| 8,562,546 B2 | 10/2013 | Shih et al. |
| 8,696,547 B2 | 4/2014 | Wibowo et al. |
| 2002/0065455 A1 | 5/2002 | Ben Haim |
| 2003/0120150 A1 | 6/2003 | Govari |
| 2004/0068178 A1 | 4/2004 | Govari |
| 2004/0215049 A1 | 10/2004 | Zdeblick et al. |
| 2006/0064038 A1 | 3/2006 | Omata et al. |
| 2007/0100332 A1 | 5/2007 | Paul et al. |
| 2007/0179381 A1 | 8/2007 | Johansson et al. |
| 2008/0015419 A1 | 1/2008 | Summers et al. |
| 2008/0270091 A1 | 10/2008 | Ramanujam et al. |
| 2009/0062642 A1 | 3/2009 | Hauck |
| 2009/0093806 A1 | 4/2009 | Govari et al. |
| 2009/0138007 A1 | 5/2009 | Govari |
| 2009/0192468 A1 | 7/2009 | Stone |
| 2010/0130878 A1 | 5/2010 | Lasso et al. |
| 2011/0054355 A1 | 3/2011 | Hunter et al. |
| 2011/0144640 A1 | 6/2011 | Heinrich et al. |
| 2011/0319791 A1 | 12/2011 | Harry et al. |
| 2012/0095305 A1 | 4/2012 | Wang et al. |
| 2012/0165702 A1 | 6/2012 | Hauck |
| 2013/0218050 A1 | 8/2013 | Eichhorn et al. |
| 2014/0371600 A1 | 12/2014 | Ji et al. |
| 2017/0340207 A1 | 11/2017 | Ludwin et al. |

FOREIGN PATENT DOCUMENTS

| | | |
|---|---|---|
| IL | 229357 A | 3/2019 |
| JP | 6320721 B2 | 4/2018 |
| WO | WO 96/05768 A1 | 2/1996 |
| WO | WO 04/012578 A2 | 2/2004 |
| WO | WO 08/157399 A1 | 12/2008 |
| WO | WO 09/029627 A1 | 3/2009 |

USING LOCATION AND FORCE MEASUREMENTS TO ESTIMATE TISSUE THICKNESS

CROSS REFERENCE TO RELATED APPLICATION

This application is a continuation of U.S. patent application Ser. No. 13/680,496, filed Nov. 19, 2012, now U.S. Patent Publication No. 2014/0142438, published May 22, 2014, the entire contents of which is incorporated herein by reference.

FIELD OF THE INVENTION

The present invention relates generally to invasive probes, and specifically to estimating tissue thickness based on location and contact force measurements received from an invasive probe.

BACKGROUND OF THE INVENTION

A wide range of medical procedures involve placing objects, such as sensors, tubes, catheters, dispensing devices and implants, within a patient's body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612, 6,332,089 and 6,690,963, in PCT International Publication WO 1996/005768, and in U.S. Patent Application Publications 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332, 2009/0093806 and U.S. Pat. No. 8,535,308, whose disclosures are incorporated herein by reference, describe methods of sensing contact pressure between the distal tip of a catheter and tissue in a body cavity using a force sensor embedded in the catheter.

Some probes include both a force sensor and a position sensor. U.S. Pat. No. 8,523,787, whose disclosure is also incorporated herein by reference, describes a method for detecting tenting in tissue (due to a force exerted by the distal tip of the probe on the tissue) using location and force measurements received from a probe that includes a position sensor and a force sensor.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

pressing a distal end of a medical probe against a wall of a body cavity;

receiving from the probe first measurements of a force exerted by the distal end on the wall;

receiving from the probe second measurements indicating a displacement of the wall in response to the force; and estimating a thickness of the wall based on the first and the second measurements.

Typically, the probe includes a catheter.

In a disclosed embodiment the method includes, prior to pressing the distal end of the probe against the wall, initializing one or more calibration matrices, each of the calibration matrices associated with a type of tissue. Typically, the type of tissue is selected from a list comprising artery tissue and endocardial tissue.

Initializing a given calibration matrix may include storing a force value, a displacement value, and an associated thickness value to each element of the calibration matrix.

In a further disclosed embodiment estimating the thickness of the wall includes identifying, in a given calibration matrix, a given element of the calibration matrix having a given force value corresponding to the first measurements and a given displacement value corresponding to the second measurements, and retrieving the thickness value from the identified matrix element.

Estimating the thickness of the wall may include interpolating between the thickness values stored in two calibration matrix elements. In one embodiment the method includes, subsequent to initializing the one or more calibration matrices and prior to estimating the thickness of the wall, selecting a given calibration matrix associated with the type of tissue corresponding to the wall of the body cavity. In another embodiment, the method includes, prior to selecting the given calibration matrix, identifying the type of tissue based on a location of the distal end.

In an alternative embodiment receiving the second measurements indicating the displacement includes receiving first position measurements from the probe indicating a first location of the probe upon the probe engaging the wall, receiving second position measurements indicating a second location of the probe upon the distal end exerting the force on the wall, and calculating a distance between the first and the second locations.

There is also provided, according to an embodiment of the present invention, medical apparatus, including:

a probe having a distal end configured for insertion into a body cavity having a wall, the probe including:

a force sensor in the distal end, configured to generate a first signal indicative of a force exerted by the distal end on the wall; and a position sensor in the distal end, configured to generate a second signal indicative of a location of the distal end within the body cavity; and a processor, which is coupled to receive and process the first and second signals from the probe so as to estimate a thickness of the wall.

There is also provided, according to an embodiment of the present invention, a computer software product, operated in conjunction with a probe that is configured for insertion into a body cavity of a patient and that includes a position sensor for measuring a position of a distal end of the probe inside the body cavity and a force sensor for measuring a force between the distal end and a wall of the body cavity, the product including a non-transitory computer-readable medium, in which program instructions are stored, which instructions, when read by a computer, cause the computer to receive from the probe, while pressing the distal end against the wall, first measurements of a force exerted by the distal end on the wall, to receive from the probe second measurements indicating a displacement of the wall in response to the force, and to estimate a thickness of the wall based on the first and the second measurements.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various diagnostic and therapeutic procedures, such as cardiac ablation and intracardiac electrical mapping, use an invasive probe, such as a catheter, whose distal tip is fitted with at least one electrode. The electrode is typically operated when the probe is pressed against a wall (also referred to herein as tissue) of a body cavity. In these procedures, it is usually important to ascertain both the precise location of the probe in the body cavity, and the force that the distal tip is exerting on the body cavity wall. Therefore, some catheters comprise position sensors for ascertaining the location of the distal tip and force sensors for measuring the force exerted by the probe on intra-body tissue, such as the endocardium.

During an ablation procedure, in embodiments of the present invention the thickness of the tissue being ablated is monitored. Applying (by the distal tip) too much force to thin tissue may cause perforation, and on the other hand, applying too little force to thicker tissue may be inefficient in isolating the tissue area electrically.

As an operator presses the distal tip of a probe against a body cavity wall, embodiments of the present invention provide methods and systems for estimating a thickness of the body cavity wall, based on location and force measurements received from sensors within the probe. The received force measurements indicate a force applied by the distal tip against the body cavity wall, and the position measurements indicate a displacement of the wall in response to the applied force. As explained in detail hereinbelow, the tissue thickness can be estimated by locating an entry in a calibration matrix with force and displacement values that correspond to the force and the displacement measurements received from the probe. Tissue thickness measurements incorporating embodiments of the present invention may be used by medical systems to replace or complement other known methods of tissue thickness measurement, such as magnetic resonance imaging (MRI) or computerized tomography (CT).

System Description

Figure 1:
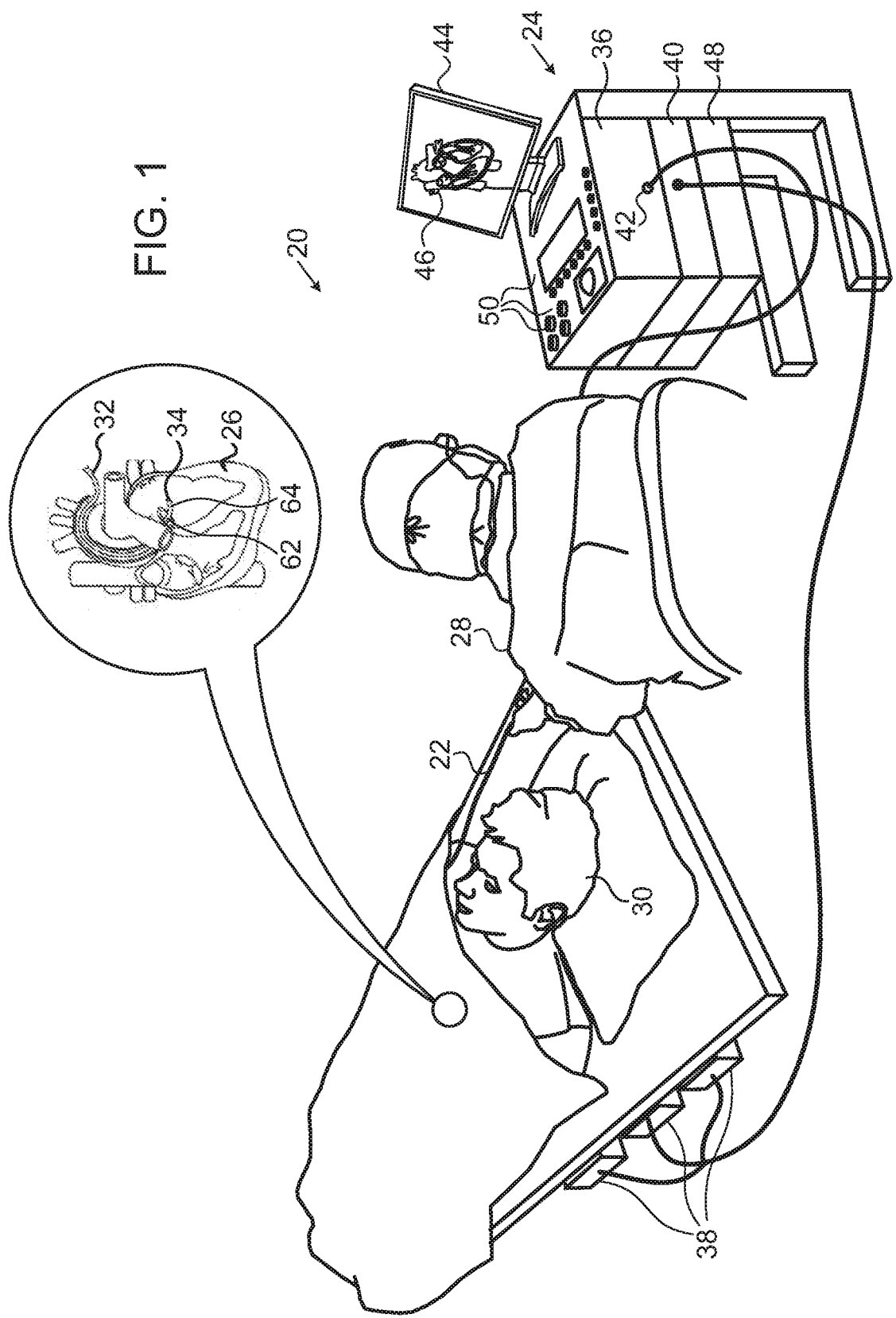
FIG. 1 is a schematic pictorial illustration of a medical system that is configured to estimate tissue thickness, in accordance with an embodiment of the present invention.

FIG. 1 is a schematic pictorial illustration of a medical system 20 that is configured to estimate tissue thickness, in accordance with an embodiment of the present invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as for mapping electrical potentials in a heart 26 or performing ablation of heart tissue. Alternatively, probe 22 may be used, mutatis mutandis, for other therapeutic and/or diagnostic purposes in the heart or in other body organs.

An operator 28, such as a cardiologist, inserts probe 22 through the vascular system of a patient 30 so that a distal end 32 of probe 22 enters a chamber of heart 26. Operator 28 advances probe 22 so that a distal tip 34 of probe 22 engages endocardial tissue at a desired location or locations. Probe 22 is typically connected by a suitable connector at its proximal end to console 24.

Console 24 typically uses magnetic position sensing to determine position coordinates of distal end 32 inside heart 26. To determine the position coordinates, a driver circuit 36 in console 24 drives field generators 38 to generate magnetic fields within the body of patient 30. Typically, field generators 38 comprise coils, which are placed below the patient's torso at known positions external to patient 30. These coils generate magnetic fields in a predefined working volume that contains heart 26. A magnetic field sensor 62 within distal end 32 of probe 22 (sensor 62 is shown in more detail in FIG. 2) generates electrical signals in response to these magnetic fields. A signal processor 40 processes these signals in order to determine the position coordinates of distal end 32, typically including both location and orientation coordinates. The method of position sensing described hereinabove is implemented in the above-mentioned CARTO™ system and is described in detail in the patents and patent applications cited above.

Signal processor 40 typically comprises a general-purpose computer, with suitable front end and interface circuits for receiving signals from probe 22 and controlling the other components of console 24. Processor 40 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 40 may be carried out by dedicated or programmable digital hardware components.

An input/output (I/O) interface 42 enables console 24 to interact with probe 22. Based on the signals received from probe 22 (via interface 42 and other components of system 20), processor 40 drives a display 44 to present operator 30 with an image 46 showing the position of distal end 32 in the patient's body, as well as status information and guidance regarding the procedure that is in progress.

In the present embodiment, processor 40 monitors measurements received from position sensor 62 and a force sensor 64 within distal end 32 (force sensor 64 is shown in more detail in FIG. 2) during periods in which the catheter is believed to be pressing against endocardial tissue of heart 26. As explained hereinbelow, when distal tip 34 is pressing against the endocardial tissue, processor 40 can determine the thickness of the tissue based on measurements received from the probe's position and force sensors.

Processor 40 stores data representing image 46 in a memory 48. In some embodiments, operator 28 can manipulate image 46 using one or more input devices 50.

Alternatively or additionally, system 20 may comprise an automated mechanism (not shown) for maneuvering and operating probe 22 within the body of patient 30. Such mechanisms are typically capable of controlling both the longitudinal motion (advance/retract) of probe 22 and transverse motion (deflection/steering) of distal end 32 of the probe. In such embodiments, processor 40 generates a control input for controlling the motion of probe 22 based on the signals provided by the magnetic field sensor in the probe.

Although FIG. 1 shows a particular system configuration, other system configurations can also be employed to implement embodiments of the present invention, and are thus considered to be within the spirit and scope of this invention. For example, the methods described hereinbelow may be applied using position transducers of types other than the magnetic field sensor described above, such as impedance-based or ultrasonic position sensors. The term "position transducer" as used herein refers to an element mounted on probe 22 which causes console 24 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Figure 2:
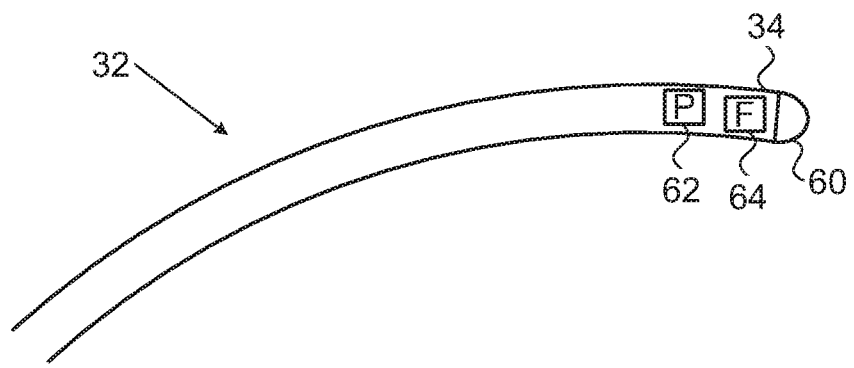
FIG. 2 is a schematic side view showing details of the distal portion of a pressure-sensitive catheter, in accordance with an embodiment of the present invention.

FIG. 2 is a schematic sectional view of distal end 32 of probe 22, in accordance with an embodiment of the present invention. Specifically, FIG. 2 shows functional elements of distal end 32 used for therapeutic and/or diagnostic activity. An electrode 60 (e.g., an ablation electrode) at distal tip 34 of the probe is typically made of a metallic material, such as a platinum/iridium alloy or another suitable material. Alternatively, multiple electrodes (not shown) along the length of the probe may be used for this purpose.

Position sensor 62 transmits a signal to console 24 that is indicative of the location coordinates of distal end 32. Position sensor 62 may comprise one or more miniature coils, and typically comprises multiple coils oriented along different axes. Alternatively, position sensor 62 may comprise either another type of magnetic sensor, an electrode which serves as a position transducer, or position transducers of other types, such as impedance-based or ultrasonic position sensors. Although FIG. 2 shows a probe with a single position sensor, embodiments of the present invention may utilize probes with more than one position sensor.

In an alternative embodiment, the roles of position sensor 62 and magnetic field generators 38 may be reversed. In other words, driver circuit 36 may drive a magnetic field generator in distal end 32 to generate one or more magnetic fields. The coils in generator 38 may be configured to sense the fields and generate signals indicative of the amplitudes of the components of these magnetic fields. Processor 40 receives and processes these signals in order to determine the position coordinates of distal end 32 within heart 26.

Force sensor 64 measures a force applied by distal tip 34 to the endocardial tissue of heart 26 by conveying a signal to the console that is indicative of the force exerted by the distal tip on the intra-body tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publication 2009/0093806 and U.S. Pat. No. 8,535,308, whose disclosures are incorporated herein by reference. Alternatively, distal end 32 may comprise another type of force sensor.

Tissue Thickness Estimation

Prior to performing a medical procedure such as cardiac ablation, probe 22 is typically calibrated using embodiments described hereinbelow. During a medical procedure, processor 40 can utilize the calibration data in order to estimate tissue thickness based on force and displacement measurements received from probe 22 (i.e., when the probe is pressing against a wall of a body cavity).

Figure 3:
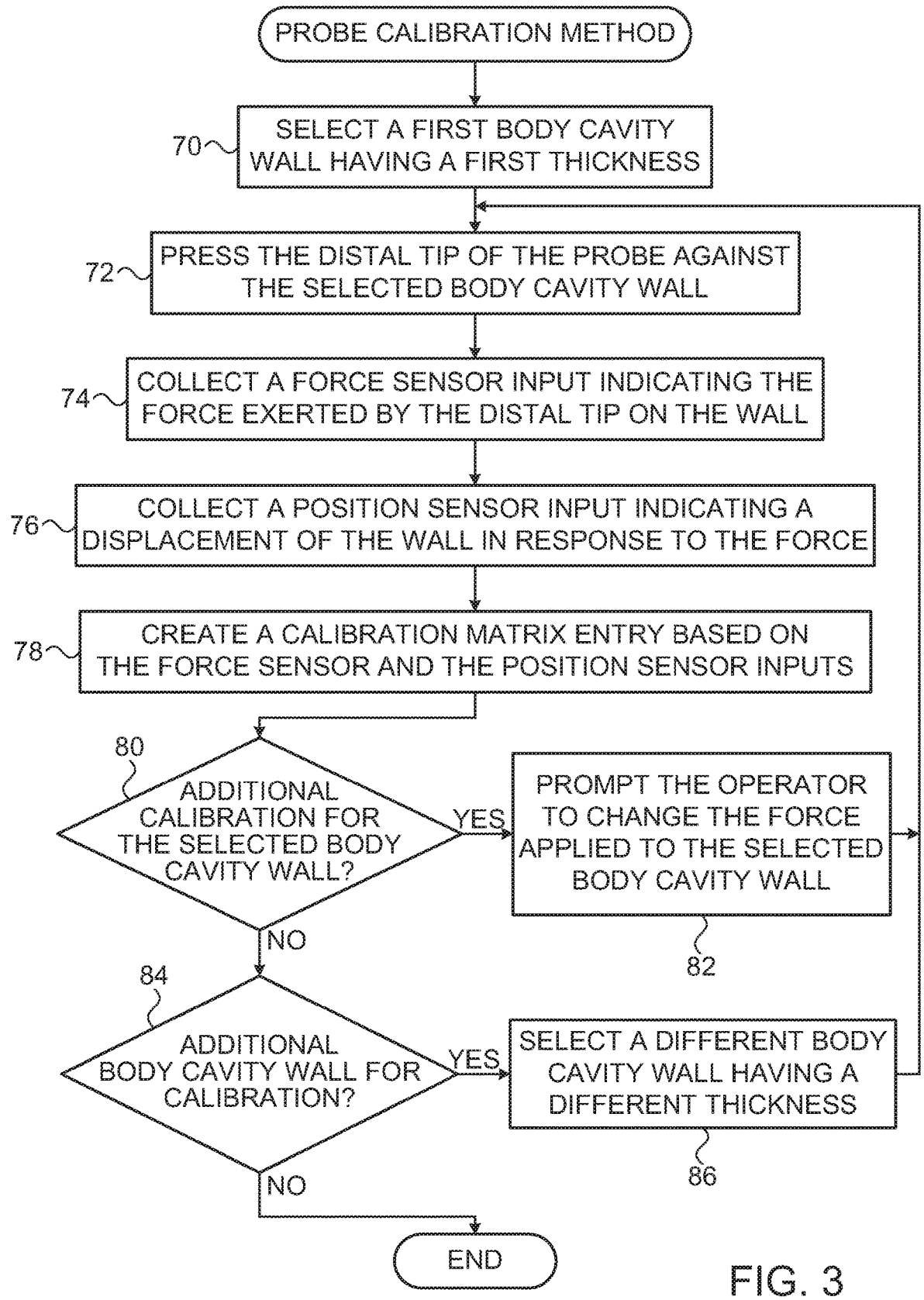
FIG. 3 is a flow diagram that schematically illustrates a method of calibrating the catheter, in accordance with an embodiment of the present invention.
Figure 4A:
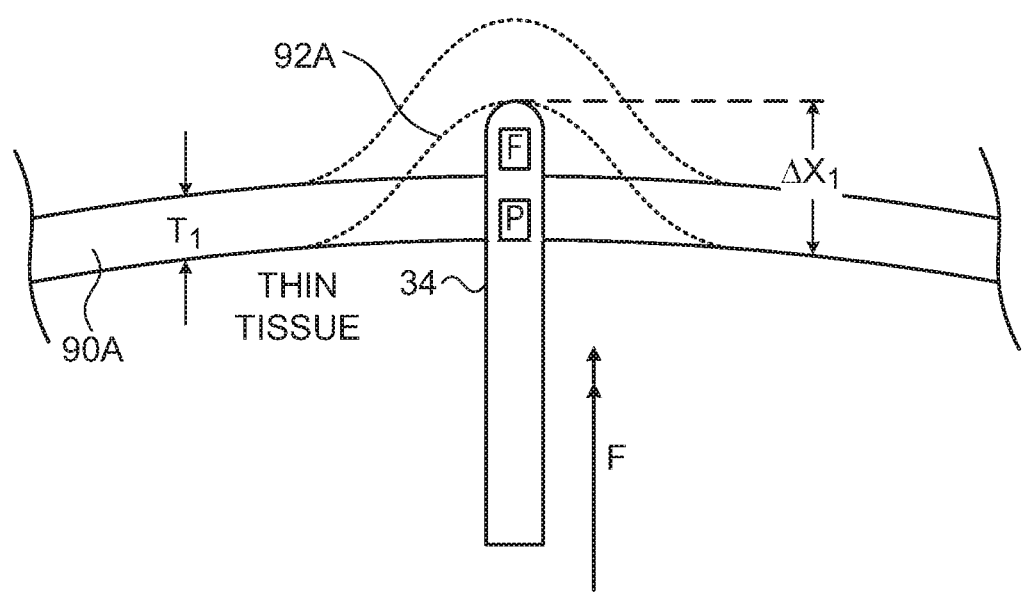
FIGS. 4A and 4B are schematic detail illustrations of tissue displacements due to a force exerted by the distal portion of the catheter on the tissue, in accordance with an embodiment of the present invention.
Figure 4B:
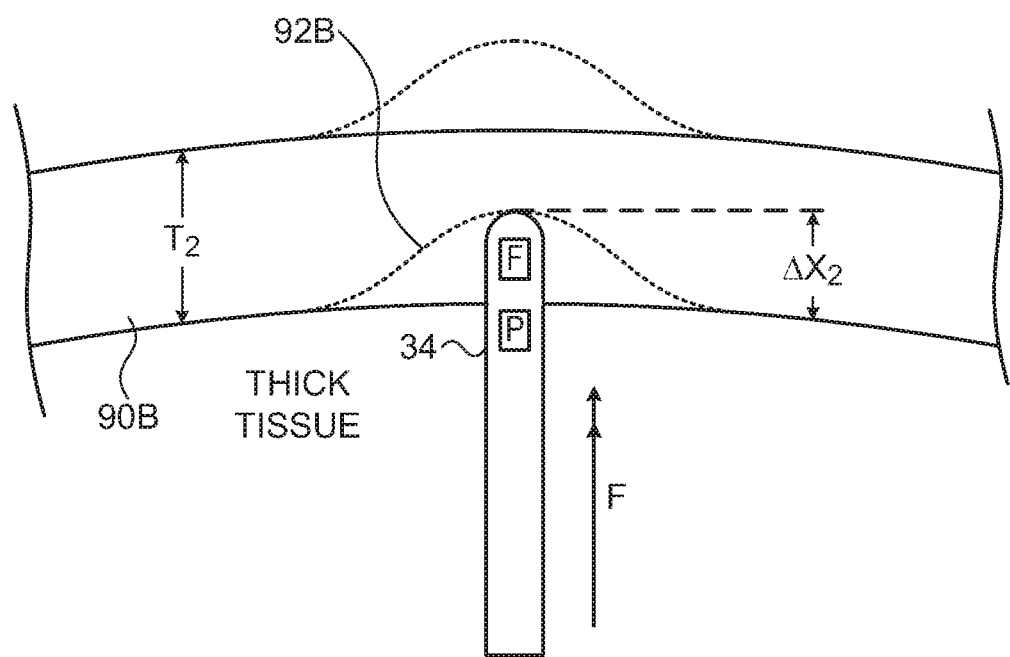

FIG. 3 is a flow diagram that schematically illustrates a method of calibrating probe 22, and FIGS. 4A and 4B are schematic detail views of displacements 92 in body cavity walls 90 in response to a force exerted by distal tip 34, in accordance with an embodiment of the present invention. In the description herein, different body cavity walls 90 and different displacements 92 may be separately identified by appending a letter to the identifying numeral, so that body cavity walls 90 comprise a body cavity wall 90A and a body cavity wall 90B, and displacements 92 comprise a displacement 92A, also indicated by $\Delta x_1$ in FIG. 4A, and a displacement 92B, also indicated by $\Delta x_2$ in FIG. 4B. Calculating $\Delta x_1$ and $\Delta x_2$ is described in detail hereinbelow.

In an initial step 70, operator 28 selects a first body cavity wall 90 having a first known thickness. In a force application step 72, the operator first positions probe 22 so that distal tip 34 engages the selected body cavity wall, and then presses the distal tip against the wall. Pressing distal tip 34 against body cavity wall 90 causes displacement 92 of wall 90 in response to the force exerted by the distal tip on the wall.

As operator 28 positions probe 22, position sensor 62 outputs a signal indicative of locations of distal tip 34. Additionally, as the operator presses distal tip 34 against the selected body cavity wall, force sensor 64 outputs a signal indicative of the force exerted by the distal tip on the wall. Both the position and the force signals, providing respective location and force measurements, are conveyed to medical system 20.

When operator 28 presses distal tip 34 against the selected body cavity wall, processor 40 collects, in a first collection step 74, a first signal from sensor 64 indicating a force exerted by the distal tip against the wall. Processor 40 also collects, in a second collection step 76, a second signal from sensor 62 indicating locations of distal tip 34. The locations indicated by the signal comprise a first location comprising where distal tip 34 initially engages the selected body cavity wall and a second location comprising a location of the distal tip after the operator presses the distal tip against the wall. Displacement 92 comprises a distance between the first location and the second location.

In a calibration step 78, processor 42 creates a calibration matrix entry based on the collected position and force measurements. To create the calibration matrix element, processor 42 maps the known thickness of body cavity wall 90 against the location measurements received from position sensor and the force measurements received from force sensor 64. Therefore, each calibration matrix element typically comprises a force value, a displacement value, and an associated thickness value. Alternatively, the thickness, force and displacement values may be stored as a range of values. For example, for a range between 1.8 and 2.0, the range of values can be stored in the calibration matrix as a lower and an upper threshold (e.g., 1.8, 2.2) of the range, or as the midpoint of the range and the value to be added to and subtracted from the midpoint (2.0, 0.2).

In a first comparison step 80, if additional calibration for the selected body cavity wall is needed to calibrate the selected body cavity wall, then in a prompting step 82, console 24 prompts operator 28 to change the force applied by distal tip 34 against the selected body cavity wall (i.e., apply lower or greater force), and the method continues with step 72. For example, to accurately calibrate a given body cavity wall, processor 40 may need to collect at least a defined number of force (and displacement) values, within a range typically used during a given medical procedure. If no additional calibration for the selected body cavity wall is needed, then in a second comparison step 84, console 24 prompts operator 28 to determine if there is an additional body cavity wall to be calibrated.

If an additional body cavity wall is needed to calibrate probe 22, then in a selection step 86, console 24 prompts operator 28 to select a different body cavity wall 90 having a different known thickness, and the method continues with step 72. The method ends when there are no additional body cavity walls needed for calibrating probe 22.

In some embodiments, operator 28 can decide if additional calibration is desired in the comparison steps described supra (i.e., in steps 80 and 84). In alternative embodiments, a software application executing on processor 40 can determine if further calibration is desired.

During calibration, operator 28 may select a variety of different types of body cavity walls 90, since different types of tissue may generate different calibration tables. For example, a specific part of the endocardium may generate a calibration matrix that differs from a calibration matrix for an artery, typically because of different elasticities of the different tissues. Sets of calibration matrices for different types of tissue can be created using the steps described hereinabove, wherein a given calibration matrix is associated with a given tissue type. In some embodiments, the set of calibration matrices can be stored to memory 48. Alternatively, the calibration matrices can be stored to a memory coupled to probe 22 (not shown).

In the examples shown in FIGS. 4A and 4B, operator 28 applies the same force vector F, as measured by force sensor 64, orthogonally to walls 90A and 90B having different thicknesses ($T_1$ and $T_2$ respectively). As described supra, processor 40 can measure the displacement in the tissue by identifying a first location of distal tip 34 when the distal tip first engages the given tissue, and identifying a second location when the force applied by the distal tip on the given tissue is F. The difference between the first location and the second location (i.e., the displacement) is $\Delta x_1$ in FIG. 4A and $\Delta x_2$ in FIG. 4B. As illustrated in the examples shown in the Figures, there is a relation between tissue thickness and tissue displacement. In other words, given the same force vector F applied by distal tip 34, the resulting displacement $\Delta x_1$ in thin body cavity wall 90A is typically greater than the displacement $\Delta x_2$ in thick body cavity wall 90B.

Figure 5:
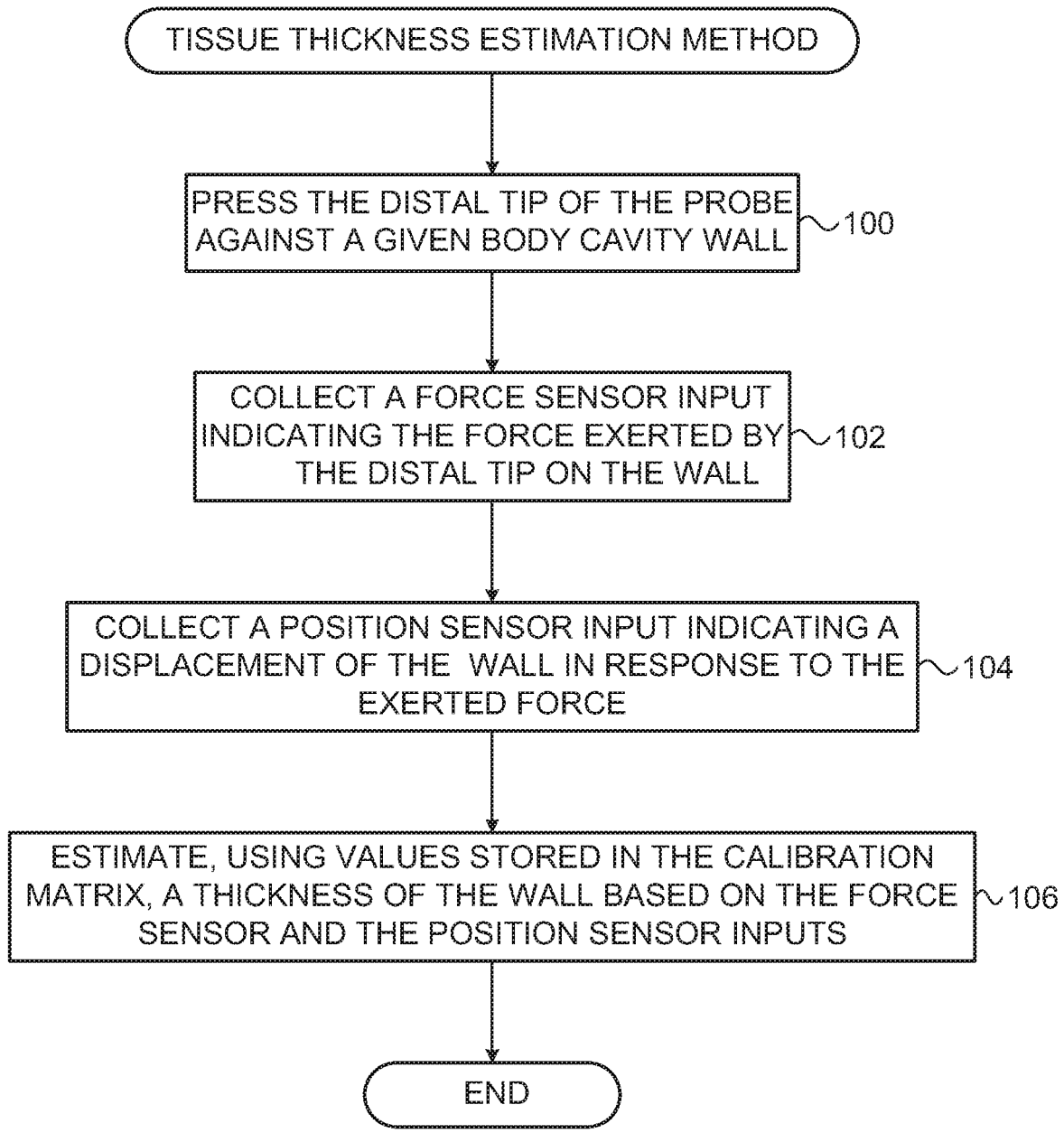
FIG. 5 is a flow diagram that schematically illustrates a method of estimating tissue thickness based on location and force measurements received from the catheter, in accordance with an embodiment of the present invention.

FIG. 5 is a schematic flow diagram that schematically illustrates a method of estimating tissue thickness based on position and force measurements conveyed by probe 22, in accordance with an embodiment of the present invention. In an initial step 100, operator 28 positions distal end 32 within a given body cavity (e.g., heart 26) and presses distal tip 34 against a given body cavity wall 90. As explained supra, there may be multiple of calibration matrices defined for different types of tissue that can be encountered during a medical procedure. Therefore, prior to pressing distal tip 34 against a given body cavity wall 90, operator 28 may identify, using input devices 50, the type of tissue in the body cavity. In response to the operator identifying the type of tissue, processor 40 can select a given calibration matrix that is associated with the identified tissue. In an alternative embodiment, processor 40 can identify the type of tissue based on the location of distal tip 34.

While operator 28 presses distal tip 34 against the given body cavity wall, processor 40 collects, in a first collection step 102, a first signal from sensor 64 indicating a force exerted by the distal tip against the wall. Processor 40 also collects, in a second collection step 104, a second signal from sensor 62 indicating locations of distal tip 34. The locations indicated by the signal comprise a first location where distal tip 34 initially engages the given body cavity wall, and a second location comprising a location of the distal tip after the operator presses the distal tip against the wall. As explained supra, displacement 92 (in response to the applied force) comprises the distance between the first location and the second location.

In an estimation step 106, processor 40 identifies an element in the calibration matrix that has force and displacement values corresponding to the collected force and the displacement measurements, and retrieves a thickness value from the identified calibration matrix element, and the method ends. In instances where corresponding values for the collected force and displacement measurements are not explicitly found in the calibration matrix, processor 40 can estimate the thickness by calculating a thickness based on an interpolation between two force and/or displacement values found in the calibration matrix.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for estimating a thickness of a body cavity wall of a patient, the method comprising:
   initializing a plurality of calibration matrices in a processor, each of the calibration matrices associated with a type of tissue;
   inserting a medical probe having a distal end which includes a position sensor through the vascular of a patient into a body cavity, the body cavity having a wall with a wall thickness;
   locating the distal end of the medical probe against a wall of the body cavity;
   generating magnetic fields, using filed generators, in a predefined working volume that is inclusive of a body cavity of the patient;
   generating, via the position sensor, first electrical signals in response to the magnetic fields, the first electrical signals indicative of first location coordinates of the distal end relative to the working volume that is inclusive of the the body cavity of the patient and transmitting these electrical signals to the processor;

identifying the type of tissue of the wall of the body cavity based on the first location coordinates of the distal tip of the probe relative to the body cavity;

pressing the distal end of the medical probe against the wall of the body cavity so as to displace the distal end;

receiving in the processor, from the probe, a first measurement of a force exerted by the distal end on the wall when the distal end of the medical probe is pressing against the wall;

generating, via the position sensor, second electrical signals in response to the magnetic fields, the second electrical signals indicative of second location coordinates of the distal end relative to the working volume that contains the body cavity and transmitting these second electrical signals to the processor; and estimating the wall thickness of the wall based on the first location coordinates and the second location coordinates, the type of tissue, and the plurality of calibration matrices.

2. The method according to claim 1, wherein the medical probe comprises a catheter.

3. The method according to claim 1 wherein generating magnetic fields using field generators comprises driving coils in the field generators, the field generators being located at known positions external to the patient.

4. The method according to claim 1, wherein the type of tissue is selected from a list comprising artery tissue and endocardial tissue.

5. The method according to claim 1, wherein initializing a given calibration matrix comprises storing a force value, a displacement value, and an associated thickness value to each element of the calibration matrix.

6. The method according to claim 5, wherein estimating the thickness of the wall comprises identifying, in a given calibration matrix, a given element of the calibration matrix having a given force value corresponding to the first location coordinates and a given displacement value corresponding to the second location coordinates, and retrieving the thickness value from the identified matrix element.

7. The method according to claim 6, wherein estimating the thickness of the wall comprises interpolating between the thickness values stored in two calibration matrix elements.

8. The method according to claim 6 further comprising, subsequent to initializing the one or more calibration matrices and prior to estimating the thickness of the wall, selecting a given calibration matrix associated with the type of tissue corresponding to the wall of the body cavity.

9. The method according to claim 8 further comprising, prior to selecting the given calibration matrix, identifying the type of tissue based on a location of the distal end.

* * * * *